US006040138A

United States Patent [19]
Lockhart et al.

[11] Patent Number: 6,040,138
[45] Date of Patent: Mar. 21, 2000

[54] EXPRESSION MONITORING BY HYBRIDIZATION TO HIGH DENSITY OLIGONUCLEOTIDE ARRAYS

[75] Inventors: David J. Lockhart, Santa Clara, Calif.; Eugene L. Brown, Newton Highlands, Mass.; Gordon G. Wong, Brookland, N.Y.; Mark S. Chee, Palo Alto; Thomas R. Gingeras, Encinitas, both of Calif.

[73] Assignee: Affymetrix, Inc., Santa Clara, Calif.

[21] Appl. No.: 08/529,115

[22] Filed: Sep. 15, 1995

[51] Int. Cl.$^7$ .............................. C12Q 1/68; C07H 21/04; C07H 21/02
[52] U.S. Cl. .......................... 435/6; 536/23.1; 536/24.3; 536/24.31; 536/24.32; 536/24.33
[58] Field of Search .................................. 435/6, 5, 91.2, 435/91.1; 536/24.3–24.33, 23.1

[56] References Cited

U.S. PATENT DOCUMENTS

| | | |
|---|---|---|
| 4,981,783 | 1/1991 | Augenlicht . |
| 5,002,867 | 3/1991 | Macevicz ..................................... 435/6 |
| 5,143,854 | 9/1992 | Pirrung et al. . |
| 5,173,260 | 12/1992 | Zander et al. . |
| 5,202,231 | 4/1993 | Drmanac et al. . |
| 5,422,241 | 6/1995 | Goldrick et al. ............................ 435/6 |
| 5,571,639 | 11/1996 | Hubbell et al. .............................. 430/5 |
| 5,690,894 | 11/1997 | Pinkel et al. ........................... 422/68.1 |
| 5,700,637 | 12/1997 | Southern et al. ........................... 435/6 |

FOREIGN PATENT DOCUMENTS

| | | |
|---|---|---|
| 0 535 242 A1 | 4/1993 | European Pat. Off. . |
| 0 717 113 | 6/1996 | European Pat. Off. . |
| 0 721 016 | 7/1996 | European Pat. Off. . |
| WO 9504594 | 2/1916 | WIPO . |
| WO 9504833 | 2/1916 | WIPO . |
| WO 9504834 | 2/1916 | WIPO . |
| WO 89/10977 | 11/1989 | WIPO . |
| WO 89/11548 | 11/1989 | WIPO . |
| WO 90/00626 | 1/1990 | WIPO . |
| WO 91/12603 | 1/1990 | WIPO . |
| WO 90 04652 | 5/1990 | WIPO . |
| WO 90/15070 | 12/1990 | WIPO . |
| WO 92/10092 | 6/1992 | WIPO . |
| WO 92 10588 | 6/1992 | WIPO . |
| WO 93/17126 | 9/1993 | WIPO . |
| WO 95 00530 | 1/1995 | WIPO . |
| WO 95/11995 | 5/1995 | WIPO . |
| WO 95/20681 | 8/1995 | WIPO . |
| WO 95/30774 | 11/1995 | WIPO . |
| WO 95/35505 | 12/1995 | WIPO . |

OTHER PUBLICATIONS

Fornace et al., 1988, Proc. Natl. Science. USA 85:8800–8804.
Fornance et al., 1984, Explt. Cell Res. 1082:61–74.
Hollbrook et al, 1991, The New Biologist 3:825–833.
Nature Biotechnology, vol. 14, No. 13, Dec. 1996, Nature Publ. Co., New York, US, pp. 1675–1680, XP002022521 D.J. Lockhart et al.: "Expression monitoring by hybridization to high–density oligonucleotide arrays".
Proc. Natl. Acad. Sci. U.S.A. (1996), 93(20), 10614–10619
CODEN: PNASA6; ISSN: 0027–8424, Oct. 1, 1996,
XP002022507 Schena, Mark et al.: "Parallel human genome analysis: microarray–based expression monitoring of 1000 genes".
Science, vol. 274, Oct. 25, 1996, AAAS, Washington, DC, US, pp. 610–614, XP002022508 M. Chee et al.: "Accessing genetic information with high–density DNA arrays".
Velculescu, V.E., et al, 1995. Serial Analysis of Gene Expression. Science 270:484–487.
Gress, T.M. et al, 1992. Hybridization Fingerprinting of High–Density cDNA–library Arrays cDNA Pools Derived from Whole Tissues, Mammalian Genome 3:609–619.
Nguyen, C. et al, 1995. Differential Gene Expression in the Murine Thymus Assayed by Quantative Hybridization of Arrayed cDNA Clones. Genomics 29–207–216.
Zhao, N. et al, 1995. High–Density cDNA Filter Analysis A Novel Approach for Large–Scale Quantitative Analysis of Gene Expression. Gene 156:207–213.
Takahashi N. et al., 1995. High–Density cDNA Filter Analysis of the Expression Profiles of the Genes Preferentially Expressed in Human Brain. Gene 164:219–227.
Schena, M. et al, 1995. Quantitative Monitoring of Gene Expression Patterns with a Complementary DNA Microarray. Science 270:467–470.
Meier–Ewert, S. et al, 1993. An Automated Approach to Generating Expressed Sequence Catalogs. Nature 361:6410: 375–376.
Eggers et al., *BioFeature*, 17:516 (1994).
Kallioniemi et al., *Science*, 258:818 (1992).
Broude et al., *Proc. Natl. Acad. Sci. USA*, 91:3072 (1994).
Fodor et al., *Research Article*, 767 (1991) ♭ page numbers?.
Lee et al., *Analytical Biochemistry*, 206:206 (1992).
Lennon et al., *Perspectives TIG October*, 7:314 (1991).
Lipshutz et al., *BioTechniques* 19:442 (1995).
Pevzner et al., *Journal of Biomolecular Structures & Dynamics*,, 9:399 (1991).
Schena et al., *Science*, 270:467 (1995).
Southern et al., *Genomics* 13:1008 (1992).
Southern et al., *Nucleic Acids Research*, 22:1368 (1994).
Stimpson et al., *Proc.Natl.Acad. Sci. USA*, 92:6379 (1995).
Lennon et al. TIG 7: 314–317, 1991.
Hoheisel TIG 10,No. 3, 1994.

*Primary Examiner*—Stephanie W. Zitomer
*Attorney, Agent, or Firm*—Townsend & Townsend & Crew

[57] ABSTRACT

This invention provides methods of monitoring the expression levels of a multiplicity of genes. The methods involve hybridizing a nucleic acid sample to a high density array of oligonucleotide probes where the high density array contains oligonucleotide probes complementary to subsequences of target nucleic acids in the nucleic acid sample. In one embodiment, the method involves providing a pool of target nucleic acids comprising RNA transcripts of one or more target genes, or nucleic acids derived from the RNA transcripts, hybridizing said pool of nucleic acids to an array of oligonucleotide probes immobilized on surface, where the array comprising more than 100 different oligonucleotides and each different oligonucleotide is localized in a predetermined region of the surface, the density of the different oligonucleotides is greater than about 60 different oligonucleotides per 1 $cm^2$, and the olignucleotide probes are complementary to the RNA transcripts or nucleic acids derived from the RNA transcripts; and quantifying the hybridized nucleic acids in the array.

45 Claims, 3 Drawing Sheets

6,040,138

EXPRESSION MONITORING BY HYBRIDIZATION TO HIGH DENSITY OLIGONUCLEOTIDE ARRAYS

BACKGROUND OF THE INVENTION

Many disease states are characterized by differences in the expression levels of various genes either through changes in the copy number of the genetic DNA or through changes in levels of transcription (e.g. through control of initiation, provision of RNA precursors, RNA processing, etc.) of particular genes. For example, losses and gains of genetic material play an important role in malignant transformation and progression. These gains and losses are thought to be "driven" by at least two kinds of genes. Oncogenes are positive regulators of tumorgenesis, while tumor suppressor genes are negative regulators of tumorgenesis (Marshall, Cell, 64: 313–326 (1991); Weinberg, Science, 254: 1138–1146 (1991)). Therefore, one mechanism of activating unregulated growth is to increase the number of genes coding for oncogene proteins or to increase the level of expression of these oncogenes (e.g. in response to cellular or environmental changes), and another is to lose genetic material or to decrease the level of expression of genes that code for tumor suppressors. This model is supported by the losses and gains of genetic material associated with glioma progression (Mikkelson et al. J. Cellular Biochm. 46: 3–8 (1991)). Thus, changes in the expression (transcription) levels of particular genes (e.g. oncogenes or tumor suppressors), serve as signposts for the presence and progression of various cancers.

Similarly, control of the cell cycle and cell development, as well as diseases, are characterized by the variations in the transcription levels of particular genes. Thus, for example, a viral infection is often characterized by the elevated expression of genes of the particular virus. For example, outbreaks of *Herpes simplex,* Epstein-Barr virus infections (e.g. infectious mononucleosis), cytomegalovirus, Varicella-zoster virus infections, parvovirus infections, human papillomavirus infections, etc. are all characterized by elevated expression of various genes present in the respective virus. Detection of elevated expression levels of characteristic viral genes provides an effective diagnostic of the disease state. In particular, viruses such as herpes simplex, enter quiescent states for periods of time only to erupt in brief periods of rapid replication. Detection of expression levels of characteristic viral genes allows detection of such active proliferative (and presumably infective) states.

Oligonucleotide probes have long been used to detect complementary nucleic acid sequences in a nucleic acid of interest (the "target" nucleic acid) and have been used to detect expression of particular genes (e.g., a Northern Blot). In some assay formats, the oligonucleotide probe is tethered, i.e., by covalent attachment, to a solid support, and arrays of oligonucleotide probes immobilized on solid supports have been used to detect specific nucleic acid sequences in a target nucleic acid. See, e.g., PCT patent publication Nos. WO 89/10977 and 89/11548. Others have proposed the use of large numbers of oligonucleotide probes to provide the complete nucleic acid sequence of a target nucleic acid but failed to provide an enabling method for using arrays of immobilized probes for this purpose. See U.S. Pat. Nos. 5,202,231 and 5,002,867 and PCT patent publication No. WO 93/17126.

The use of "traditional" hybridization protocols for monitoring or quantifying gene expression is problematic. For example two or more gene products of approximately the same molecular weight will prove difficult or impossible to distinguish in a Northern blot because they are not readily separated by electrophoretic methods. Similarly, as hybridization efficiency and cross-reactivity varies with the particular subsequence (region) of a gene being probed it is difficult to obtain an accurate and reliable measure of gene expression with one, or even a few, probes to the target gene.

The development of VLSIPS™ technology provided methods for synthesizing arrays of many different oligonucleotide probes that occupy a very small surface area. See U.S. Pat. No. 5,143,854 and PCT patent publication No. WO 90/15070. U.S. patent application Ser. No. 082,937, filed Jun. 25, 1993, describes methods for making arrays of oligonucleotide probes that can be used to provide the complete sequence of a target nucleic acid and to detect the presence of a nucleic acid containing a specific nucleotide sequence.

Prior to the present invention, however, it was unknown that high density oligonucleotide arrays could be used to reliably monitor message levels of a multiplicity of preselected genes in the presence of a large abundance of other (non-target) nucleic acids (e.g., in a cDNA library, DNA reverse transcribed from an mRNA, mRNA used directly or amplified, or polymerized from a DNA template). In addition, the prior art provided no rapid and effective method for identifying a set of oligonucleotide probes that maximize specific hybridization efficacy while minimizing cross-reactivity nor of using hybridization patterns (in particular hybridization patterns of a multiplicity of oligonucleotide probes in which multiple oligonucleotide probes are directed to each target nucleic acid) for quantification of target nucleic acid concentrations.

SUMMARY OF THE INVENTION

The present invention is premised, in part, on the discovery that microfabricated arrays of large numbers of different oligonucleotide probes (DNA chips) may effectively be used to not only detect the presence or absence of target nucleic acid sequences, but to quantify the relative abundance of the target sequences in a complex nucleic acid pool. In particular, prior to this invention it was unknown that hybridization to high density probe arrays would permit small variations in expression levels of a particular gene to be identified and quantified in a complex population of nucleic acids that out number the target nucleic acids by 1,000 fold to 1,000,000 fold or more.

Thus, this invention provides for a method of simultaneously monitoring the expression (e.g. detecting and or quantifying the expression) of a multiplicity of genes. The levels of transcription for virtually any number of genes may be determined simultaneously. Typically, at least about 10 genes, preferably at least about 100, more preferably at least about 1000 and most preferably at least about 10,000 different genes are assayed at one time.

The method involves providing a pool of target nucleic acids comprising mRNA transcripts of one or more of said genes, or nucleic acids derived from the mRNA transcripts; hybridizing the pool of nucleic acids to an array of oligonucleotide probes immobilized on a surface, where the array comprises more than 100 different oligonucleotides, each different oligonucleotide is localized in a predetermined region of said surface, the density of the different oligonucleotides is greater than about 60 different oligonucleotides per 1 $cm^2$, and the olignucleotide probes are complementary to the mRNA transcripts or nucleic acids derived from the mRNA transcripts; and quantifying the hybridized nucleic acids in the array. In a preferred embodiment, the pool of target nucleic acids is one in which the concentration of the target nucleic acids (mRNA transcripts or nucleic acids derived from the mRNA transcripts) is proportional to the expression levels of genes encoding those target nucleic acids.

In a preferred embodiment, the array of oligonucleotide probes is a high density array comprising greater than about 100, preferably greater than about 1,000 more preferably greater than about 16,000 and most preferably greater than about 65,000 or 250,000 or even 1,000,000 different oligonucleotide probes. Such high density arrays comprise a probe density of generally greater than about 60, more generally greater than about 100, most generally greater than about 600, often greater greater than about 1000, more often greater than about 5,000, most often greater than about 10,000, preferably greater than about 40,000 more preferably greater than about 100,000, and most preferably greater than about about 400,000 different oligonucleotide probes per $cm^2$. The oligonucleotide probes range from about 5 to about 50 nucleotides, more preferably from about 10 to about 40 nucleotides and most preferably from about 15 to about 40 nucleotides in length. The array may comprise more than 10, preferably more than 50, more preferably more than 100, and most preferably more than 1000 oligonucleotide probes specific for each target gene. Although a planar array surface is preferred, the array may be fabricated on a surface of virtually any shape or even a multiplicity of surfaces.

The array may further comprise mismatch control probes. Where such mismatch controls are present, the quantifying step may comprise calculating the difference in hybridization signal intensity between each of the oligonucleotide probes and its corresponding mismatch control probe. The quantifying may further comprise calculating the average difference in hybridization signal intensity between each of the oligonucleotide probes and its corresponding mismatch control probe for each gene.

The probes present in the high density array can be oligonucleotide probes selected according to the optimization methods described below. Alternatively, non-optimal probes may be included in the array, but the probes used for quantification (analysis) can be selected according to the optimization methods described below.

Oligonucleotide arrays for the practice of this invention are preferably synthesized by light-directed very large scaled immobilized polymer synthesis (VLSIPS) as described herein. The array includes test probes which are oligonucleotide probes each of which has a sequence that is complementary to a subsequence of one of the genes (or the mRNA or the corresponding antisense cRNA) whose expression is to be detected. In addition, the array can contain normalization controls, mismatch controls and expression level controls as described herein.

The pool of nucleic acids may be labeled before, during, or after hybridization, although in a preferred embodiment, the nucleic acids are labeled before hybridization. Fluorescence labels are particularly preferred and, where used, quantification of the hybridized nucleic acids is by quantification of fluorescence from the hybridized fluorescently labeled nucleic acid. Such quantification is facilitated by the use of a fluorescence microscope which can be equipped with an automated stage to permit automatic scanning of the array, and which can be equipped with a data acquisition system for the automated measurement recording and subsequent processing of the fluorescence intensity information.

In a preferred embodiment, hybridization is at low stringency (e.g. about 20° C. to about 50° C., more preferably about 30° C. to about 40° C., and most preferably about 37° C. and 6X SSPE-T or lower) with at least one wash at higher stringency. Hybridization may include subsequent washes at progressively increasing stringency until a desired level of hybridization specificity is reached.

The pool of target nucleic acids can be the total $polyA^+$ mRNA isolated from a biological sample, or cDNA made by reverse transcription of the RNA or second strand cDNA or RNA transcribed from the double stranded cDNA intermediate. Alternatively, the pool of target nucleic acids can be treated to reduce the complexity of the sample and thereby reduce the background signal obtained in hybridization. In one approach, a pool of mRNAs, derived from a biological sample, is hybridized with a pool of oligonucleotides comprising the oligonucleotide probes present in the high density array. The pool of hybridized nucleic acids is then treated with RNase A which digests the single stranded regions. The remaining double stranded hybridization complexes are then denatured and the oligonucleotide probes are removed, leaving a pool of mRNAs enhanced for those mRNAs complementary to the oligonucleotide probes in the high density array.

In another approach to background reduction, a pool of mRNAs derived from a biological sample is hybridized with paired target specific oligonucleotides where the paired target specific oligonucleotides are complementary to regions flanking subsequences of the mRNAs complementary to the oligonucleotide probes in the high density array. The pool of hybridized nucleic acids is treated with RNase H which digests the hybridized (double stranded) nucleic acid sequences. The remaining single stranded nucleic acid sequences which have a length about equivalent to the region flanked by the paired target specific oligonucleotides are then isolated (e.g. by electrophoresis) and used as the pool of nucleic acids for monitoring gene expression.

Finally, a third approach to background reduction involves eliminating or reducing the representation in the pool of particular preselected target mRNA messages (e.g., messages that are characteristically overexpressed in the sample). This method involves hybridizing an oligonucleotide probe that is complementary to the preselected target mRNA message to the pool of $polyA^+$ mRNAs derived from a biological sample. The oligonucleotide probe hybridizes with the particular preselected $polyA^+$ mRNA (message) to which it is complementary. The pool of hybridized nucleic acids is treated with RNase H which digests the double stranded (hybridized) region thereby separating the message from its $polyA^+$ tail. Isolating or amplifying (e.g., using an oligo dT column) the $polyA^+$ mRNA in the pool then provides a pool having a reduced or no representation of the preselected target mRNA message.

It will be appreciated that the methods of this invention can be used to monitor (detect and/or quantify) the expression of any desired gene of known sequence or subsequence. Moreover, these methods permit monitoring expression of a large number of genes simultaneously and effect significant advantages in reduced labor, cost and time. The simultaneous monitoring of the expression levels of a multiplicity of genes permits effective comparison of relative expression levels and identification of biological conditions characterized by alterations of relative expression levels of various genes. Genes of particular interest for expression monitoring include genes involved in the pathways associated with various pathological conditions (e.g., cancer) and whose expression is thus indicative of the pathological condition.

Such genes include, but are not limited to the HER2 (c-erbB-2/neu) proto-oncogene in the case of breast cancer, receptor tyrosine kinases (RTKs) associated with the etiology of a number of tumors including carcinomas of the breast, liver, bladder, pancreas, as well as glioblastomas, sarcomas and squamous carcinomas, and tumor suppressor genes such as the P53 gene and other "marker" genes such as RAS, MSH2, MLH1 and BRCA1. Other genes of particular interest for expression monitoring are genes involved in the immune response (e.g., interleukin genes), as well as genes involved in cell adhesion (e.g., the integrins or selectins) and signal transduction (e.g., tyrosine kinases), etc.

In another embodiment, this invention provides for a method of selecting a set of oligonucleotide probes, that specifically bind to a target nucleic acid (e.g., a gene or genes whose expression is to be monitored or nueleic acids derived from the gene or its transcribed mRNA). The method involves providing a high density array of oligonucleotide probes where the array comprises a multiplicity of probes wherein each probe is complementary to a subsequence of the target nucleic acid. The target nucleic acid is then hybridized to the array of oligonucleotide probes to identify and select those probes where the difference in hybridization signal intensity between each probe and its mismatch control is detectable (preferably greater than about 10% of the background signal intensity, more preferably greater than about 20% of the background signal intensity and most preferably greater than about 50% of the background signal intensity). The method can further comprise hybridizing the array to a second pool of nucleic acids comprising nucleic acids other than the target nucleic acids; and identifying and selecting probes having the lowest hybridization signal and where both the probe and its mismatch control have a hybridization intensity equal to or less than about 5 times the background signal intensity, preferably equal to or less than about 2 times the background signal intensity, more preferably equal to or less than about 1 times the background signal intensity, and most preferably equal or less than about half the background signal intensity.

In a preferred embodiment, the multiplicity of probes can include every different probe of length n that is complementary to a subsequence of the target nucleic acid. The probes can range from about 10 to about 50 nucleotides in length. The array is preferably a high density array as described above. Similarly, the hybridization methods, conditions, times, fluid volumes, detection methods are as described above and herein below.

In addition, this invention provides for a composition comprising an array of oligonucleotide probes immobilized on a substrate, where the array comprises more than 100 different oligonucleotides and each different oligonucleotide is localized in a predetermined region of the solid support and the density of the array is greater than about 60 different oligonucleotides per 1 cm$^2$ of substrate. The oligonucleotide probes are specifically hybridized to one or more fluorescently labeled nucleic acids such that the fluorescence in each region of the array is indicative of the level of expression of each of a multiplicity of preselected genes. The array is preferably a high density array as described above and may further comprise expression level controls, mismatch controls and normalization controls as described herein.

Finally, this invention provides for kits for simultaneously monitoring expression levels of a multiplicity of genes. The kits include an array of immobilized oligonucleotide probes complementary to subsequences of the multiplicity of target genes, as described above. In one embodiment, the array comprises at least 100 different oligonucleotide probes and the density of the array is greater than about 60 different oligonucleotides per 1 cm$^2$ of surface. The kit may also include instructions describing the use of the array for detection and/or quantification of expression levels of the multiplicity of genes. The kit may additionally include one or more of the following: buffers, hybridization mix, wash and read solutions, labels, labeling reagents (enzymes etc.), "control" nucleic acids, software for probe selection, array reading or data analysis and any of the other materials or reagents described herein for the practice of the claimed methods.

Definitions

The phrase "massively parallel screening" refers to the simultaneous screening of at least about 100, preferably about 1000, more preferably about 10,000 and most preferably about 1,000,000 different nucleic acid hybridizations.

The terms "nucleic acid" or "nucleic acid molecule" refer to a deoxyribonucleotide or ribonucleotide polymer in either single-or double-stranded form, and unless otherwise limited, would encompass known analogs of natural nucleotides that can function in a similar manner as naturally occurring nucleotides.

An oligonucleotide is a single-stranded nucleic acid ranging in length from 2 to about 500 bases.

As used herein a "probe" is defined as an oligonucleotide capable of binding to a target nucleic acid of complementary sequence through one or more types of chemical bonds, usually through complementary base pairing, usually through hydrogen bond formation. As used herein, an oligonucleotide probe may include natural (ie. A, G, C, or T) or modified bases (7-deazaguanosine, inosine, etc.). In addition, the bases in oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages.

The term "target nucleic acid" refers to a nucleic acid (often derived from a biological sample), to which the oligonucleotide probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from context.

"Subsequence" refers to a sequence of nucleic acids that comprise a part of a longer sequence of nucleic acids.

The term "complexity" is used here according to standard meaning of this term as established by Britten et al. *Methods of Enzymol.* 29:363 (1974). See, also *Cantor and Schimmel Biophysical Chemistry: Part III* at 1228–1230 for further explanation of nucleic acid complexity.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotides). Stringent conditions may also be achieved with the addition of destabjiig agents such as formamide.

The term "mismatch control" refers to a probe that has a sequence deliberately selected not to be perfectly complementary to a particular target sequence. The mismatch control typically has a corresponding test probe that is perfectly complementary to the same particular target sequence. The mismatch may comprise one or more bases. While the mismatch(es) may be locates anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g. probes directed to nucleic acids of the opposite sense or to genes not found in the sample such as bacterial genes where the sample is mammalian nucleic acids). Background can also be calculated as the average signal intensity produced by regions of the array that lack any probes at all.

The term "quantifying" when used in the context of quantifiing transcription levels of a gene can refer to absolute or to relative quantification. Absolute quantification may be accomplished by inclusion of known concentration (s) of one or more target nucleic acids (e.g. control nucleic acids such as Bio B or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

BRIEF DESCRIPTION OF THE DRAWINGS

FIGS. 1A and 1B show the hybridization intensity of IL4 RNA hybridized to the high density array of Example 1.

FIG. 1B expands the ordinate of FIG. 1A to show the low concentration values.

FIGS. 1C and 1D show hybridization intensity plotted as a function of target RNA for a collection of different target RNAs. The graphs show the average values of the 1000 highest intensity probes.

FIG. 1D expands the ordinate of FIG. 1C to show the low concentration values.

DETAILED DESCRIPTION

Figure 1:
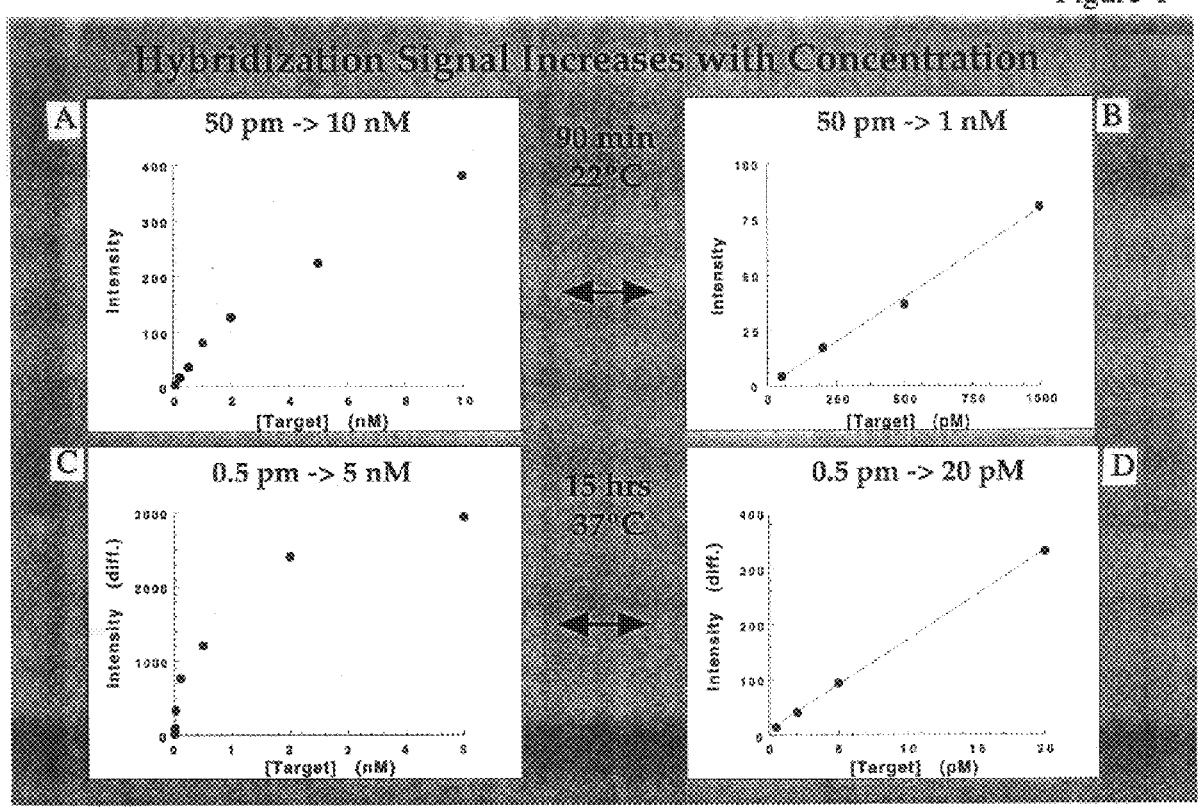
FIGS. 1A–1D show plots of hybridization intensity plotted as a function of concentration of target mRNA.

This invention provides methods of monitoring (detecting and/or quantifying) the expression levels of one or more genes. The methods involve hybridization of a nucleic acid target sample to a high density array of nucleic acid probes and then quantifying the amount of target nucleic acids hybridized to each probe in the array.

While nucleic acid hybridization has been used for some time to determine the expression levels of various genes (e.g., Northern Blot), it was a surprising discovery of this invention that high density arrays are suitable for the quantification of the small variations in expression (transcription) levels of a gene in the presence of a large population of heterogenous nucleic acids. The signal may be present at a concentration of less than about 1 in 1,000, and is often present at a concentration less than 1 in 10,000 more preferably less than about 1 in 50,000 and most preferably less than about 1 in 100,000 or even 1 in 1,000,000.

Prior to this invention, it was expected that hybridization of such a complex mixture to a high density array might overwhelm the available probes and make it impossible to detect the presence of low-level target nucleic acids. It was thus unclear that a low level signal could be isolated and detected in the presence of misleading signals due to cross-hybridization and non-specific binding both to substrate and probe.

It was a surprising discovery that, to the contrary, high density arrays are particularly well suited for monitoring expression of a multiplicity of genes and provide a level of sensitivity and discrimination hitherto unexpected.

Preferred high density arrays of this invention comprise greater than about 100, preferably greater than about 1000, more preferably greater than about 16,000 and most preferably greater than about 65,000 or 250,000 or even greater than about 1,000,000 different oligonucleotide probes. The oligonucleotide probes range from about 5 to about 50 nucleotides, more preferably from about 10 to about 40 nucleotides and most preferably from about 15 to about 40 nucleotides in length.

The location and sequence of each different oligonucleotide probe sequence in the array is known. Moreover, the large number of different probes occupies a relatively small area providing a high density array having a probe density of generally greater than about 60, more generally greater than about 100, most generally greater than about 600, often greater greater than about 1000, more often greater than about 5,000, most often greater than about 10,000, preferably greater than about 40,000 more preferably greater than about 100,000, and most preferably greater than about about 400,000 different oligonucleotide probes per $cm^2$. The small surface area of the array (often less than about 10 $cm^2$, preferably less than about 5 $cm^2$ more preferably less than about 2 $cm^2$, and most preferably less than about 1.6 $cm^2$) permits extremely uniform hybridization conditions (temperature regulation, salt content, etc.) while the extremely large number of probes allows massively parallel processing of hybridizations.

It was a discovery of this invention that the use of high density arrays for expression monitoring provides a number of advantages not found with other methods. For example, the use of large numbers of different probes that specifically bind to the transcription product of a particular target gene provides a high degree of redundancy and internal control that permits optimization of probe sets for effective detection of particular target genes and minimizes the possibility of errors due to cross-reactivity with other nucleic acid species.

Apparently suitable probes often prove ineffective for expression monitoring by hybridization. For example, certain subsequences of a particular target gene may be found in other regions of the genome and probes directed to these subsequences will cross-hybridize with the other regions and not provide a signal that is a meaningful measure of the expression level of the target gene. Even probes that show little cross reactivity may be unsuitable because they generally show poor hybridization due to the formation of structures that prevent effective hybridization. Finally, in sets with large numbers of probes, it is difficult to identify hybridization conditions that are optimal for all the probes in a set. Because of the high degree of redundancy provided by the large number of probes for each target gene, it is possible to eliminate those probes that function poorly under a given set of hybridization conditions and still retain enough probes to a particular target gene to provide an extremely sensitive and reliable measure of the expression level (transcription level) of that gene.

In addition, the use of large numbers of different probes to each target gene makes it possible to monitor expression of families of closely-related nucleic acids. The probes may be selected to hybridize both with subsequences that are conserved across the family and with subsequences that differ in the different nucleic acids in the family. Thus, hybridization with such arrays permits simultaneous monitoring of the various members of a gene family even where the various genes are approximately the same size and have high levels of homology. Such measurements are difficult or impossible with traditional hybridization methods.

Because the high density arrays contain such a large number of probes it is possible to provide numerous controls including, for example, controls for variations or mutations in a particular gene, controls for overall hybridization conditions, controls for sample preparation conditions, controls for metabolic activity of the cell from which the nucleic acids are derived and mismatch controls for non-specific binding or cross hybridization.

Finally, because of the small area occupied by the high density arrays, hybridization may be carried out in extremely small fluid volumes (e.g., 250 μl or less, more preferably 100 μl or less, and most preferably 10 μl or less). In small volumes, hybridization may proceed very rapidly. In addition, hybridization conditions are extremely uniform throughout the sample, and the hybridization format is amenable to automated processing.

This invention demonstrates that hybridization with high density oligonucleotide probe arrays provides an effective means of monitoring expression of a multiplicity of genes. In addition this invention provides for methods of sample treatment and array designs and methods of probe selection that optimize signal detection at extremely low concentrations in complex nucleic acid mixtures.

The expression monitoring methods of this invention may be used in a wide variety of circumstances including detection of disease, identification of differential gene expression between two samples (e.g., a pathological as compared to a healthy sample), screening for compositions that upregulate or downregulate the expression of particular genes, and so forth.

In one preferred embodiment, the methods of this invention are used to monitor the expression (transcription) levels of nucleic acids whose expression is altered in a disease state. For example, a cancer may be characterized by the overexpression of a particular marker such as the HER2 (c-erbB-2/neu) proto-oncogene in the case of breast cancer. Similarly, overexpression of receptor tyrosine kinases (RTKs) is associated with the etiology of a number of tumors including carcinomas of the breast, liver, bladder, pancreas, as well as glioblastomas, sarcomas and squamous carcinomas (see Carpenter, *Ann. Rev. Biochem.*, 56: 881–914 (1987)). Conversely, a cancer (e.g., colerectal, lung and breast) may be characterized by the mutation of or underexpression of a tumor suppressor gene such as P53 (see, e.g., Tominaga et al. *Critical Rev. in Oncogenesis*, 3: 257–282 (1992)).

The materials and methods of this invention are typically used to monitor the expression of a multiplicity of different genes simultaneously. Thus, in one embodiment, the invention provide for simultaneous monitoring of at least about 10, preferably at least about 100, more preferably at least about 1000 and most preferably at least about 10,000 different genes.

I. Methods of monitoring gene expression

Generally the methods of monitoring gene expression of this invention involve (1) providing a pool of target nucleic acids comprising RNA transcript(s) of one or more target gene(s), or nucleic acids derived from the RNA transcript(s); (2) hybridizing the nucleic acid sample to a high density array of probes (including control probes); and (3) detecting the hybridized nucleic acids and calculating a relative expression (transcription) level.

A) Providing a nucleic acid sample.

One of skill in the art will appreciate that in order to measure the transcription level (and thereby the expression level) of a gene or genes, it is desirable to provide a nucleic acid sample comprising mRNA transcript(s) of the gene or genes, or nucleic acids derived from the mRNA transcript(s).

As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

In a particularly preferred embodiment, where it is desired to quantify the transcription level (and thereby expression) of a one or more genes in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript is desired, no elaborate control or calibration is required.

In the simplest embodiment, such a nucleic acid sample is the total mRNA isolated from a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The nucleic acid (either genomic DNA or mRNA) may be isolated from the sample according to any of a number of methods well known to those of skill in the art. One of skill will appreciate that where alterations in the copy number of a gene are to be detected genomic DNA is preferably isolated. Conversely, where expression levels of a gene or genes are to be detected, preferably RNA (mRNA) is isolated.

Methods of isolating total mRNA are well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993) and Chapter 3 of *Laboratory Techniques in Biochemistry and Molecular Biology: Hybridization with Nucleic Acid Probes, Part I. Theory and Nucleic Acid Preparation*, P. Tijssen, ed. Elsevier, N.Y. (1993)).

In a preferred embodiment, the total nucleic acid is isolated from a given sample using, for example, an acid guanidinium-phenol-chloroform extraction method and polyA$^+$ mRNA is isolated by oligo dT column chromatography or by using (dT)n magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skdll in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis, et al., *PCR Protocols. A guide to Methods and Application*. Academic Press, Inc. San Diego, (1990)), ligase chain reaction (LCR) (see Wu and Wallace, *Genomics*, 4: 560 (1989), Landegren, et al., *Science*, 241: 1077 (1988) and Barringer, et al., *Gene*, 89: 117 (1990), transcription amplification (Kwoh, et al., *Proc. Natl. Acad. Sci. USA*, 86: 1173 (1989)), and self-sustained sequence replication (Guatelli, et al., *Proc. Nat. Acad. Sci. USA*, 87: 1874 (1990)).

In a particularly preferred embodiment, the sample mRNA is reverse transcribed with a reverse transcriptase and a promer consisting of oligo dT and a sequence encoding the phage T7 promoter to provide single stranded DNA template. The second DNA strand is polymerized using a DNA polymerase. After synthesis of double-stranded cDNA, 17 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.) and this particular method is described in detail by Van Gelder, et al., *Proc. Natl. Acad. Sci. USA*, 87: 1663–1667 (1990) who demonstrate that in vitro amplification according to this method preserves the relative frequencies of the various RNA transcripts. Moreover, Eberwine et al. *Proc. Natl. Acad. Sci. USA*, 89: 3010–3014 provide a protocol that uses two rounds of amplification via in vtro transcription to achieve greater than $10^6$ fold amplification of the original starting material thereby permiting expression monitoring even where biological samples are limited.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lamda vectors designed for Cre-loxP plasmid subcloning (see e.g., Palazzolo et al., *Gene*, 88: 25–36 (1990)).

In a particularly preferred embodiment, a high activity RNA polymerase (e.g. about 2500 units/$\mu$L for T7, available from Epicentre Technologies) is used.

B) Labeling nucleic acids.

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., DynabeadsTM), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

C) Modifying sample to improve signal/noise ratio.

The nucleic acid sample may be modified prior to hybridization to the high density probe array in order to reduce sample complexity thereby decreasing background signal and improving sensitivity of the measurement. In one embodiment, complexity reduction is achieved by selective degradation of background mRNA. This is accomplished by hybridizing the sample mRNA (e.g., polyA$^+$ RNA) with a pool of DNA oligonucleotides that hybridize specifically with the regions to which the probes in the array specifically hybridize. In a preferred embodiment, the pool of oligonucleotides consists of the same probe oligonucleotides as found on the high density array.

The pool of oligonucleotides hybridizes to the sample mRNA forming a number of double stranded (hybrid duplex) nucleic acids. The hybridized sample is then treated with RNase A, a nuclease that specifically digests single stranded RNA. The RNase A is then inhibited, using a protease and/or commercially available RNase inhibitors, and the double stranded nucleic acids are then separated from the digested single stranded RNA. This separation may be accomplished in a number of ways well known to those of skill in the art including, but not limited to, electrophoresis, and gradient centrifugation. However, in a preferred embodiment, the pool of DNA oligonucleotides is provided attached to beads forming thereby a nucleic acid affinity column. After digestion with the RNase A, the hybridized DNA is removed simply by denaturing (e.g., by adding heat or increasing salt) the hybrid duplexes and washing the previously hybridized mRNA off in an elution buffer.

The undigested mRNA fragments which will be hybridized to the probes in the high density array are then preferably end-labeled with a fluorophore attached to an RNA linker using an RNA ligase. This procedure produces a labeled sample RNA pool in which the nucleic acids that do not correspond to probes in the array are eliminated and thus unavailable to contribute to a background signal.

Another method of reducing sample complexity involves hybridizing the mRNA with deoxyoligonucleotides that hybridize to regions that border on either size the regions to which the high density array probes are directed. Treatment with RNAse H selectively digests the double stranded (hybrid duplexes) leaving a pool of single-stranded mRNA corresponding to the short regions (e.g., 20 mer) that were formerly bounded by the deoxyolignucleotide probes and which correspond to the targets of the high density array probes and longer mRNA sequences that correspond to regions between the targets of the probes of the high density array. The short RNA fragments are then separated from the long fragments (e.g., by electrophoresis), labeled if necessary as described above, and then are ready for hybridization with the high density probe array.

In a third approach, sample complexity reduction involves the selective removal of particular (preselected) mRNA messages. In particular, highly expressed mRNA messages that are not specifically probed by the probes in the high density array are preferably removed. This approach involves hybridizing the polyA$^+$ mRNA with an oligonucleotide probe that specifically hybridizes to the preselected message close to the 3' (poly A) end. The probe may be selected to provide high specificity and low cross reactivity. Treatment of the hybridized message/probe complex with RNase H digests the double stranded region effectively removing the polyA$^+$ tail from the rest of the message. The sample is then treated with methods that specifically retain or amplify polyA$^+$ RNA (e.g., an oligo dT column or (dT)n magnetic beads). Such methods will not retain or amplify the selected message(s) as they are no longer associated with a polyA$^+$ tail. These highly expressed messages are effectively removed from the sample providing a sample that has reduced background mRNA.

II. Hybridization Arrav Design

A) Probe composition

One of skill in the art will appreciate that an enormous number of array designs are suitable for the practice of this invention. The high density array will typically include a number of probes that specifically hybridize to the nucleic acid expression of which is to be detected. In addition, in a preferred embodiment, the array will include one or more control probes.

1) Test probes

In its simplest embodiment, the high density array includes "test probes". These are oligonucleotides that range from about 5 to about 50 nucleotides, more preferably from about 10 to about 40 nucleotides and most preferably from about 15 to about 40 nucleotides in length. These oligonucleotide probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as 1) Normalization controls; 2) Expression level controls; and 3) Mismatch controls.

2) Normalization controls.

Normalization controls are oligonucleotide probes that are perfectly complementary to labeled reference oligonucleotides that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalzzation control(s) can also be selected to reflect the (average) base composition of the other probes in the array, however in a preferred embodiment, only one or a few normalization probes are used and they are selected such that they hybridize well (i.e. no secondary structure) and do not match any target-specific probes.

Normalization probes can be localized at any position in the array or at multiple positions throughout the array to control for spatial variation in hybridization efficiently. In a preferred embodiment, the normalzzation controls are located at the comers or edges of the array as well as in the middle.

3) Exiression level controls.

Expression level controls are probes that hybridize specifically with constitutively expressed genes in the biological sample. Expression level controls are designed to control for the overall health and metabolic activity of a cell. Examination of the covariance of an expression level control with the expression level of the target nucleic acid indicates whether measured changes or variations in expression level of a gene is due to changes in transcription rate of that gene or to general variations in health of the cell. Thus, for example, when a cell is in poor health or lacing a critical metabolite the expression levels of both an active target gene and a constitutively expressed gene are expected to decrease. The converse is also true. Thus where the expression levels of both an expression level control and the target gene appear to both decrease or to both increase, the change may be attributed to changes in the metabolic activity of the cell as a whole, not to differential expression of the target gene in question. Conversely, where the expression levels of the target gene and the expression level control do not covary, the variation in the expression level of the target gene is attributed to differences in regulation of that gene and not to overall variations in the metabolic activity of the cell.

Virtually any constitutively expressed gene provides a suitable target for expression level controls. Typically expression level control probes have sequences complementary to subsequences of constitutively expressed "housekeeping genes" including, but not limited to the β-actin gene, the transferrin receptor gene, the GAPDH gene, and the like.

4) Mismatch controls.

Mismatch controls may also be provided for the probes to the target genes, for expression level controls or for normalization controls. Mismatch controls are oligonucleotide probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed. Mismatch probes thus indicate whether a hybridization is specific or not. For example, if the target is present the perfect match probes should be consistently brighter than the mismatch probes. In addition, if all central mismatches are present, the mismatch probes can be used to detect a mutation. Finally, it was also a discovery of the present invention that the difference in intensity between the perfect match and the mismatch probe (I(PM)-I(MM)) provides a good measure of the concentration of the hybridized material.

5) Sample preparation/amplification controls

The high density array may also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/amplification control probe is directed before processing. Quantification of the hybridization of the sample preparation/amplification control probe then provides a measure of alteration in the abundance of the nucleic acids caused by processing steps (e.g. PCR, reverse transcription, in idtro transcription, etc.).

B) "Test Probe" Selection and Optimization.

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20 mer sequence complementary to an IL-2 mRNA.

There, however, may exist 20 mer subsequences that are not unique to the IL-2 mRNA. Probes directed to these subsequences are expected to cross hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

Thus, in one embodiment, this invention provides for a method of optimizing a probe set for detection of a particular gene. Generally, this method involves providing a high density array containing a multiplicity of probes of one or more particular length(s) that are complementary to subsequences of the mRNA transcribed by the target gene. In one embodiment the high density array may contain every probe of a particular length that is complementary to a particular mRNA. The probes of the high density array are then hybridized with their target nucleic acid alone and then hybridized with a high complexity, high concentration nucleic acid sample that does not contain the targets complementary to the probes. Thus, for example, where the target nucleic acid is an RNA, the probes are first hybridized with their target nucleic acid alone and then hybridized with RNA made from a cDNA library (e.g., reverse transcribed polyA$^+$ mRNA) where the sense of the hybridized RNA is opposite that of the target nucleic acid (to insure that the high complexity sample does not contain targets for the probes). Those probes that show a strong hybridization signal with their target and little or no cross-hybridization with the high complexity sample are preferred probes for use in the high density arrays of this invention.

The high density array may additionally contain mismatch controls for each of the probes to be tested. In a preferred embodiment, the mismatch controls contain a central mismatch. Where both the mismatch control and the target probe show high levels of hybridization (e.g., the hybridization to the mismatch is nearly equal to or greater than the hybridization to the corresponding test probe), the test probe is preferably not used in the high density array.

In a particularly preferred embodiment, optimal probes are selected according to the following method: First, as indicated above, an array is provided containing a multiplicity of oligonucleotide probes complementary to subsequences of the target nucleic acid. The oligonucleotide probes may be of a single length or may span a variety of lengths ranging from 5 to 50 nucleotides. The high density array may contain every probe of a particular length that is complementary to a particular mRNA or may contain probes selected from various regions of particular mRNAs. For each target-specific probe the array also contains a mismatch control probe; preferably a central mismatch control probe.

The oligonucleotide array is hybridized to a sample containing target nucleic acids having subsequences complementary to the oligonucleotide probes and the difference in hybridization intensity between each probe and its mismatch control is determined. Only those probes where the difference between the probe and its mismatch control exceeds a threshold hybridization intensity (e.g. preferably greater than 10% of the background signal intensity, more preferably greater than 20% of the background signal intensity and most preferably greater than 50% of the background signal intensity) are selected. Thus, only probes that show a strong signal compared to their mismatch control are selected.

The probe optimization procedure can optionally include a second round of selection. In this selection, the oligonucleotide probe array is hybridized with a nucleic acid sample that is not expected to contain sequences complementary to the probes. Thus, for example, where the probes are complementary to the RNA sense strand a sample of antisense RNA is provided. Of course, other samples could be provided such as samples from organisms or cell lines known to be lacking a particular gene, or known for not expressing a particular gene.

Only those probes where both the probe and its mismatch control show hybridization intensities below a threshold value (e.g. less than about 5 times the background signal intensity, preferably equal to or less than about 2 times the background signal intensity, more preferably equal to or less than about 1 times the background signal intensity, and most preferably equal or less than about half background signal intensity) are selected. In this way probes that show minimal non-specific binding are selected. Finally, in a preferred embodiment, the n probes (where n is the number of probes desired for each target gene) that pass both selection criteria and have the highest hybridization intensity for each target gene are selected for incorporation into the array, or where already present in the array, for subsequent data analysis. Of course, one of skill in the art, will appreciate that either selection criterion could be used alone for selection of probes.

III. Synthesis of High Density Arrays

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 which disclose methods of forming vast arrays of peptides, oligonucleotides and other molecules using, for example, light-directed synthesis techniques. See also, Fodor et al., *Science*, 251, 767–77 (1991). These procedures for synthesis of polymer arrays are now referred to as VLSIPS™ procedures. Using the VLSIPS™ approach, one heterogenous array of polymers is converted, through simultaneous coupling at a number of reaction sites, into a different heterogenous array. See, U.S. application Ser. Nos. 07/796,243 and 07/980,523.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Serial No. 08/082,937, filed Jun. 25, 1993 describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatiied with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854.

Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

In addition to the foregoing, additional methods which can be used to generate an array of oligonucleotides on a single substrate are described in co-pending applications Ser. No. 07/980,523, filed Nov. 20, 1992, and 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

IV. Hybridization

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6X SSPE-T at 37° C. (0.005% Triton X-100) to ensure hybridization and then subsequent washes are performed at higher stringency (e.g., 1 X SSPE-T at 37° C.) to eliminate mismatched hybrid duplexes. Successive washes may be performed at increasingly higher stringency (e.g., down to as low as 0.25 X SSPE-T at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra.)

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology, Vol.* 24: *Hybridization With Nucleic Acid Probes,* P. Tijssen, ed. Elsevier, N.Y., (1993)).

V. Signal Detection

Means of detecting labeled target (sample) nucleic acids hybridized to the probes of the high density array are known to those of skill in the art. Thus, for example, where a colorimetric label is used, simple visualization of the label is sufficient. Where a radioactive labeled probe is used, detection of the radiation (e.g with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototransducer (e.g., a photomultiplier, a solid state array, a ccd camera, etc.) attached to an automated data acquisition system to automatically record the fluorescence signal produced by hybridization to each oligonucleotide probe on the array. Such automated systems are described at length in U.S. Pat. No: 5,143,854, PCT application 20 92/10092, and copending U.S. Ser. No. 08/195,889 filed on Feb. 10, 1994. Use of laser illumination in conjunction with automated confocal microscopy for signal detection permits detection at a resolution of better than about 100 4m, more preferably better than about 50 μm, and most preferably better than about 25 μm.

VI. Signal Evaluation

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of florescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1pM) will show a very weak signal. At some low level of concentration, the signal becomes virtually indistinguishable from background. In evaluating the hybridization data, a threshold intensity value may be selected below which a signal is not counted as being essentially indistinguishable from background.

Where it is desirable to detect nucleic acids expressed at lower levels, a lower threshold is chosen. Conversely, where only high expression levels are to be evaluated a higher threshold level is selected. In a preferred embodiment, a suitable threshold is about 10% above that of the average background signal.

In addition, the provision of appropriate controls permits a more detailed analysis that controls for variations in hybridization conditions, cell health, non-specific binding and the like. Thus, for example, in a preferred embodiment, the hybridization array is provided with normalization controls as described above in Section II.A.2. These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Typically, normalization is accomplished by dividing the measured signal from the other probes in the array by the average signal produced by the normalization controls. Normalization may also include correction for variations due to sample preparation and amplification. Such normalization may be accomplished by dividing the measured signal by the average signal from the sample preparation/amplfication control probes (e.g., the Bio B probes). The resulting values may be multiplied by a constant value to scale the results.

As indicated above, the high density array can include mismatch controls. In a preferred embodiment, there is a mismatch control having a central mismatch for every probe (except the normalization controls) in the array. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control both show high signals, or the mismatch shows a higher signal than its corresponding test probe, there is a problem with the hybridization and the signal from those probes is ignored. The difference in hybridization signal intensity between the target specific probe and its corresponding mismatch control is a measure of the discrimination of the target-specific probe. Thus, in a preferred embodiment, the signal of the mismatch probe is subtracted from the signal from its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored. The expression level of a particular gene can then be scored by the number of positive signals (either absolute or above a threshold value), the intensity of the positive signals (either absolute or above a selected threshold value), or a combination of both metrics (e.g., a weighted average).

It is a surprising discovery of this invention, that normalization controls are often unnecessary for useful quantification of a hybridization signal. Thus, where optimal probes have been identified in the two step selection process as described above, in Section II.B., the average hybridization signal produced by the selected optimal probes provides a good quantified measure of the concentration of hybridized nucleic acid.

VII. Monitoring Expression Levels

As indicated above, the methods of this invention may be used to monitor expression levels of a gene in a wide variety of contexts. For example, where the effects of a drug on gene expression is to be determined the drug will be administered to an organism, a tissue sample, or a cell. Nucleic acids from the tissue sample, cell, or a biological sample from the organism and from an untreated organism tissue sample or cell are isolated as described above, hybridized to a high density probe array containing probes directed to the gene of interest and the expression levels of that gene are determined as described above.

Similarly, where the expression levels of a disease marker (e.g., P53, RTK, or HER2) are to be detected (e.g., for the diagnosis of a pathological condition in a patient), comparison of the expression levels of the disease marker in the sample to disease markers from a healthy organism will reveal any deviations in the expression levels of the marker in the test sample as compared to the healthy sample. Correlation of such deviations with a pathological condition provides a diagnostic assay for that condition.

EXAMPLES

The following examples are offered to illustrate, but not to limit the present invention.

Example 1

Detection of the Expression Levels of Target Genes

Experiments were designed to evalutate the specificity of hybridization, the relationship between hybridization signal and concentration of target nucleic acid, and the quantifiability of RNA detection at low concentration levels. These experiments involved hybridizing labeled RNA from a number of preselected genes (IL-2, IL-3, IL4, IL-6, IL-10, IL-12p40, GM-CSF, IFN-γ, TNF-α, mCTLA8, β-actin, GAPDH, IL-11 receptor, and Bio B) to a high density oligonucleotide probe array comprising a large number of probes complementary to subsequences of these genes (see, Section B, below for a description of the array) in the presence or absence of an RNA sample transcribed from a cDNA library. The target genes were hybridized to the high density probe array either individually, together, or individually or together in the presence of labeled RNA transcribed from a murine cDNA library as described below.

A) Preparation of labeled RNA.

1) From each of the preselected genes

Fourteen genes (IL-2, IL-3, Il-4, IL-6, Il -10, IL-12p40, GM-CSF, IFN-γ, TNF-α, CTLA8, β-actin, GAPDH, IL-11 receptor, and Bio B) were each cloned into the p Bluescript II KS (+) phagemid (Stratagene, La Jolla, Calif., USA). The orientation of the insert was such that T3 RNA polymerase gave sense transcripts and T7 polymerase gave antisense RNA.

In vitro transcription was done with cut templates in a manner like that described by Melton et al., *Nucleic Acids Research,* 12: 7035–7056 (1984). A typical in vitro transcription reaction used 5 μg DNA template, a buffer such as that included in Ambion's Maxiscript in vitro Transcription Kit (Ambion Inc., Huston, Tex., USA) and GTP (3 mM), ATP (1.5 mM), UTP and fluoresceinated UTP (3 mM total, UTP: Fl-UTP 1:1) and CTP and fluoresceinated CTP (2 mM total, CTP: FI-CTP, 3:1). Reactions done in the Ambion buffer had 20 mM DTT and RNase inhibitor. The T7 polymerase was a high concentration polymerase (activity about 2500 units/IL) available from Epicentre Technologies, Madison, Wis., USA. The reaction was run from 1.5 to about 8 hours.

The nucleotide triphosphates were removed using a microcon-100 or Pharmacia microspin S-200 column. The labeled RNA was then fragmented in a pH 8.1 Tris-HCl buffer containing 30 mM Mg(OAc)$_2$ at 94° C. for 30 to 40 minutes depending on the length of the RNA transcript.

2) From cDNA libraries.

Labeled RNA was produced from one of two murine cell lines; T10, a B cell plasmacytoma which was known not to express the genes (except IL-10, actin and GAPDH) used as target genes in this study, and 2D6, an IL-12 growth dependent T cell line (Th$_1$ subtype) that is known to express most of the genes used as target genes in this study. Thus, RNA derived from the T10 cell line provided a good total RNA baseline mixture suitable for spiling with known quantities of RNA from the particular target genes. In contrast, mRNA derived from the 2D6 cell line provided a good positive control providing typical endogenously transcribed amounts of the RNA from the target genes.

To produce the T10 cDNA library, cDNA was directionally cloned into λSHlox-1 (GibcoBRL, Gaithersburg, Md., USA) at EcoRi/HInd III to give a phage library. The phage library was converted to a plasmid library using "automatic Cre-loxP" plasmid subcloning according to the method of Palazzolo, et al., *Gene,* 88: 25–36 (1990). After this the DNA was linearized with Not I and T7 polymerase was used to generate labeled T10 RNA in an in vitro transcription reaction as described above.

Labeled 2D6 mRNA was produced by directionally cloning the 2D6 cDNA with αZipLox, NotI-SalI arms available from GibcoBRL in a manner similar to T10. The linearired pZ11 library was transcribed with T7 to generate sense RNA as described above.

B) High Density Array Preparation

A high density array of 20 mer oligonucleotide probes was produced using VLSIPS technology. The high density array included the oligonucleotide probes as listed in Table 1. A central mismatch control probe was provided for each gene-specific probe resulting in a high density array containing over 16,000 different oligonucleotide probes.

TABLE 1

High density array design. For every probe there was also a mismatch control having a central 1 base mismatch.

| Probe Type | Target Nucleic Acid | Number of Probes |
|---|---|---|
| Test Probes: | IL-2 | 691 |
| | IL-3 | 751 |
| | IL-4 | 361 |
| | IL-6 | 691 |
| | IL-10 | 481 |
| | IL-12p40 | 911 |
| | GM-CSF | 661 |
| | IFN-γ | 991 |
| | TNF-α | 641 |
| | mCTLA8 | 391 |
| | IL-11 receptor | 158 |
| House Keeping Genes: | GAPDH | 388 |
| | β-actin | 669 |

TABLE 1-continued

High density array design. For every probe there was also a mismatch control having a central 1 base mismatch.

| Probe Type | Target Nucleic Acid | Number of Probes |
|---|---|---|
| Bacterial gene (sample preparation/amplification control) | Bio B | 286 |

The high density array was synthesized on a planar glass slide.

C) Hybridization conditions.

The RNA transcribed from cDNA was then hybridized to the high density oligonucleotide probe array at low stringency (e.g., in 6 X SSPE-T with 0.5 mg/ml unlabeled, degraded herring sperm DNA as a blocking agent, at 37° C. for 18 hours). The hybridized arrays were washed under progressively more stringent conditions, (e.g., in 1 X SSPE-T at 37° C. for 7 minutes down to 0.25 X SSPE-T overnight) with the hybridized array being read by a laser-illuminated scanning confocal fluorescence microscope between washes.

It was discovered that the excess RNA in the sample frequently bound up the high density array probes and/or targets and apparently prevented the probes from specifically binding with their intended target. This problem was obviated by hybridizing at temperatures over 30° C. and/or adding CTAB (cetyltrimethylammonium bromide) a detergent.

D) Optimization of Probe Selection

In order to optimize probe selection for each of the target genes, the high density array of oligonucleotide probes was hybridized with the mixture of labeled RNAs transcribed from each of the target genes. Fluorescence intensity at each location on the high density array was determined by scanning the high density array with a laser illuminated scanning confocal fluorescence microscope connected to a data acquisition system.

Probes were then selected for further data analysis in a two-step procedure. First, in order to be counted, the difference in intensity between a probe and its corresponding mismatch probe had to exceed a threshold limit (50 counts, or about half background, in this case). This eliminated from consideration probes that did not hybridize well and probes for which the mismatch control hybridizes at an intensity comparable to the perfect match.

The high density array was hybridized to a labeled RNA sample which, in principle, contains none of the sequences on the high density array. In this case, the oligonucleotide probes were chosen to be complementary to the sense RNA. Thus, an anti-sense RNA population should have been incapable of hybridizing to any of the probes on the array. Where either a probe or its mismatch showed a signal above a threshold value (100 counts above background) it was not included in subsequent analysis.

Then, the signal for a particular gene was counted as the average difference (perfect match—mismatch control) for the selected probes for each gene.

D) Interpretation of results

1) Specificity of Hybridization

In order to evaluate the specificity of hybridization, the high density array described above was hybridized with 50 pM of the RNA sense strand of IL-2, IL-3, IL-4, IL-6, Actin, GAPDH and Bio B or IL-10, IL-12p40, GM-CSF, IFN-γ, TNF-α, mCTLA8 and Bio B. The hybridized array showed strong specific signals for each of the test target nucleic acids with minimal cross hybridization.

2) Relationship between Target Concentration and Hybridization Signal

In order to evaluate the relationship between hybridization signal and target probe concentration, hybridization intensity was measured as a function of concentration of the RNAs for one or more of the target genes. FIG. 1 shows the results of this experiment. Graphs A and B are plots of the hybridization intensity of high concentrations (50 pM to 10 nM) of IL4 hybridized to the array for 90 minutes at 22° C. Plot B merely expands the ordinate of plot A to show the low concentration values. In both plots, the hybridization signal increases with target concentration and the signal level is proportional to the RNA concentration between 50 pM and 1 nM.

Graphs C and D are plots of the average hybridization intensity differences of the 1000 most intense probes when the array is hybridized, for 15 hours at 37° C., to a mixture of 0.5 pM to 20 pM each of labeled RNA from IL-2, IL-3, IL4, IL-6, IL-10, GM-CSF, IFN-γ, TNF-α, mCTLA8, β-actin, GAPDH, and Bio B. Even a signal, in effect, averaged across 13 different target RNAs, shows an intensity proportional to target RNA concentration. Again, Graph D expands the ordinate of plot A to show the low concentration signal.

At high target nucleic acid concentration, the hybridization time could be decreased, while at lower target nucleic acid concentration, the hybridization time should be increased. By varying hybridization time, it is possible to obtain a substantially linear relationship between target RNA concentration and hybridization intensity for a wide range of target RNA concentrations.

3) Detection of Gene Expression levels in a complex target sample.

In order to evaluate the ability of the high density array described above to measure variations in expression levels of the target genes, hybridization was performed with the T10 murine library RNA, the library spiked with 10 pM each of mCTLA8, IL-6, IL-3, IFN-γ, and IL-12 and 50 pM of each of these RNA transcripts prepared as described above.

Because simply spildng the RNA mixture with the selected target genes and then immediately hybridizing might provide an artificially elevated reading relative to the rest of the mixture, the spiked sample was treated to a series of procedures to mitigate differences between the library RNA and the added RNA. Thus the "spike" was added to the sample which was then heated to 37° C. and annealed. The sample was then frozen, thawed, boiled for 5 minutes, cooled on ice and allowed to return to room temperature before performing the hybridization.

The sample was then hybridized at low stringency and washed at progressively higher stringency as described above. The best probes for each target gene were selected as described above, in Section D, and the average intensity of the difference (perfect match—mismatch) of the probes for each target gene is plotted in FIGS. 2 and 3.

Figure 2:
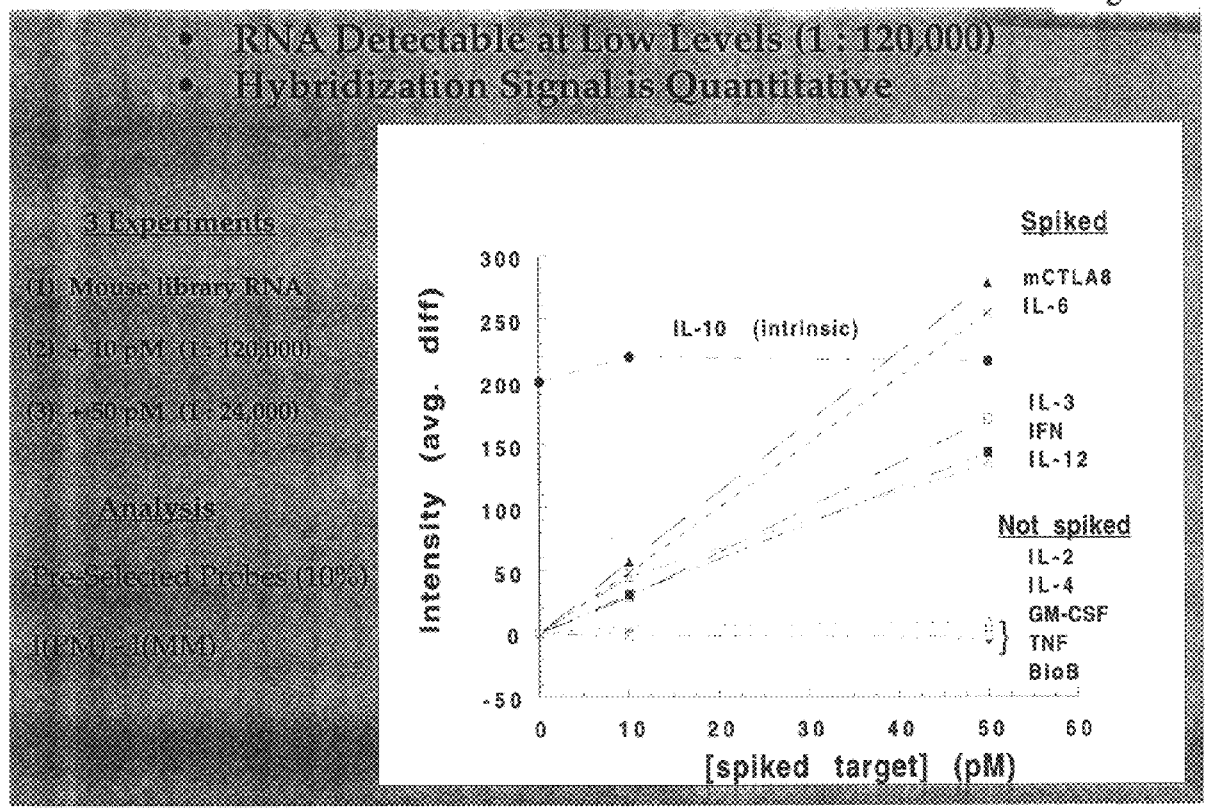
FIG. 2 shows a plot of hybridization intensity for mouse library RNA, mouse library RNA spiked with mCTLA8, IL-6, IL-3, IFN-γ, and IL-12p40 at 10 pM or 50 pM. The data presented is based upon approximately the best (optimal) 10% of the probes to each gene, where the optimal probes are selected according to the method disclosed herein.

A 50 pM spike represents a target mRNA concentration of about 1 in 24,000, while a 10 pM spike represents a target mRNA concentration of about 1 in 120,000. As illustrated in FIG. 2, the high density array easily resolves and quantifies the relative expression levels of each of the target genes in one simultaneous hybridization. Moreover, the relative expression level is quantifiable with a 5 fold difference in concentration of the target mRNA resulting in a 3 to 6 fold difference in hybridization intensity for the five spiked targets.

Figure 3:
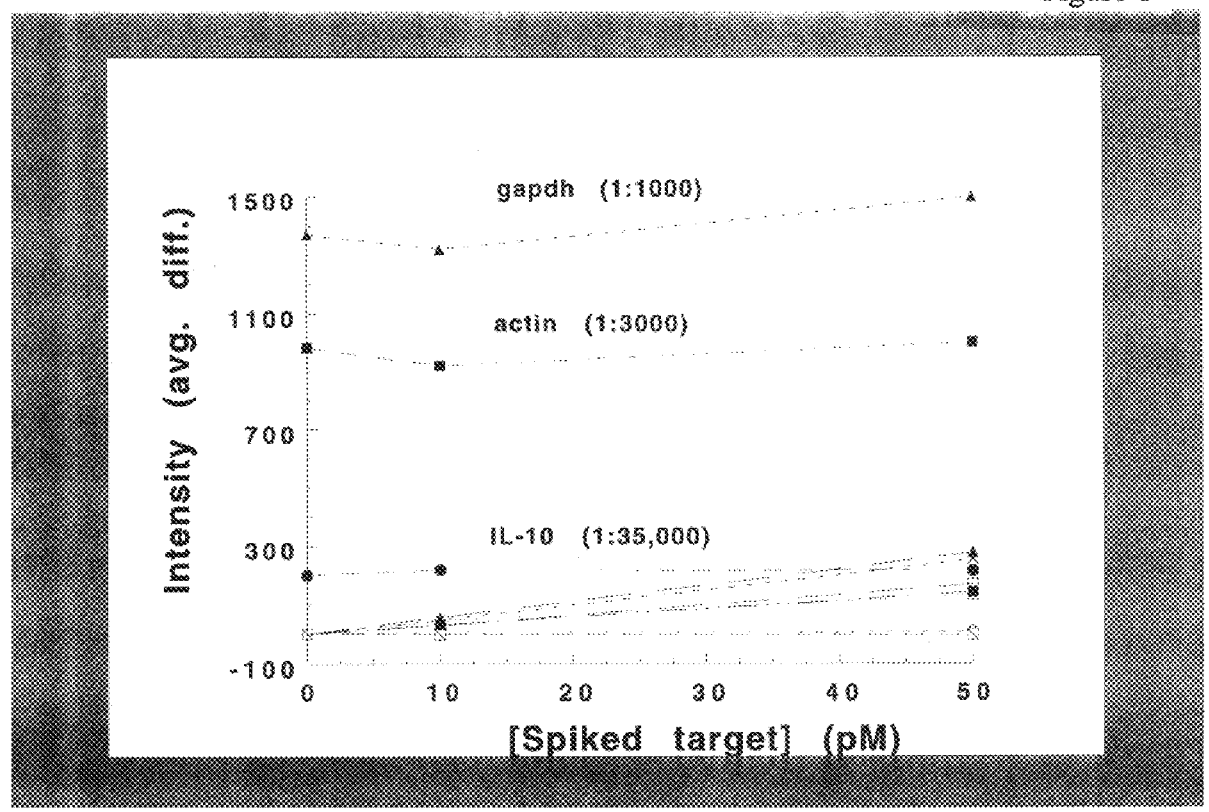
FIG. 3 shows a plot of the data from Example 1 (FIG. 2) with the ordinate condensed to show the constitutively expressed GAPDH and Actin genes and the intrinsic expressed IL-10 gene.

FIG. 3 replots FIG. 2 on a condensed scale so that the expression levels of constitutively expressed GAPDH and Actin and the level of IL-10 which is endogenously expressed by the cell line, is visible. It is notable that the single hybridization to the array resolved expression levels varying from 1 in 1000 for GAPDH to 1 in 124,000 for the spiked mRNAs without the high concentration RNA (the RNA library) overwhelming the signal from the genes expressed at low levels (e.g., IL-10).

It is also worthy of note that the endogenous (intrinsic) IL-10 was transcribed at a level comparable to or lower than the spiked RNAs (see FIG. 2) and the method thus is capable of quantifying the levels of transcription of genes that are transcribed at physiologically realistic levels.

The method described herein thus easily quantifies changes in RNA concentrations of 5 to 10 fold. Detection is highly specific and quantitative at levels as low as 1 in 120,000. The sensitivity and specificity is sufficient to detect low concentration RNAs (comparable to about 20 to 30 per cell) in the presence of total mammalian cell message populations. Other experiments have detected concentrations as low as 1 in 300,000, comparable to about 10 RNAs per cell and the method clearly provides a means for simultaneously screening transcription levels of literally hundreds of genes simultaneously in a complex RNA pool.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of analyzing the expression of one or more genes, said method comprising:
   (a) providing a pool of target nucleic acids comprising RNA transcripts of one or more of said genes, or nucleic acids derived therefrom using said RNA transcripts as templates;
   (b) hybridizing said pool of tarzet nucleic acids to an array of oligonucleotide probes immobilized on a surface, said array comprising more than 100 different oligonucleotides, at least some of which comprise control probes, wherein each different oligonucleotide is localized in a predetermined region of said surface, the density of said different oligonucleotides is greater than about 60 different oligonucleotides per 1 $cm^2$, and at least some of said oligonucleotide probes are complementary to said RNA transcripts or said nucleic acids derived therefrom using said RNA transcripts; and
   (c) quantifying the hybridization of said nucleic acids to said array, wherein said quantification is proportional to the expression level of said genes.

2. The method of claim 1, wherein said array of oligonucleotides further comprises mismatch control probes.

3. The method of claim 2, wherein said quantifying comprises calculating the difference in hybridization signal intensity between each of said oligonucleotide probes and its corresponding mismatch control probe.

4. The method of claim 3, wherein said quantifying comprises calculating the average difference in hybridization signal intensity between each of said oligonucleotide probes and its corresponding mismatch control probe for each gene.

5. The method of claim 1, wherein hybridization and quantification is accomplished in under 48 hours.

6. The method of claim 1, wherein said multiplicity of genes is 100 genes or more.

7. The method of claim 1, wherein for each gene, said array comprises at least 10 different oligonucleotide probes complementary to subsequences of that gene.

8. The method of claim 1, wherein said hybridization is performed with a fluid volume of about 250 $\mu$l or less.

9. The method of claim 1, wherein said quantifying comprises detecting a hybridization signal that is proportional to the concentration of said RNA in said nucleic acid sample.

10. The method of claim 1, wherein said oligonucleotides are from 5 to about 50 nucleotides in length.

11. The method of claim 1, wherein said oligonucleotides are synthesized by light-directed polymer synthesis.

12. The method of claim 1, wherein said control probes comprise sequences from constitutively expressed control genes.

13. The method of claim 12, wherein said control genes are selected from the group consisting of β-actin, GAPDH, and the transferrin receptor.

14. The method of claim 1, wherein said hybridization comprises a hybridization at low stringency of 30° C. to 50° C. and 6 X SSPE-T or lower and a wash at higher stringency.

15. The method of claim 1, wherein said pool of target nucleic acids is a pool of mRNAs.

16. The method of claim 1, wherein said pool of target nucleic acids is a pool of RNAs in vitro transcribed from a pool of cDNAs.

17. The method of claim 1, wherein said pool of target nucleic acids is amplified from a biological sample by an in vivo or an in vitro method.

18. The method of claim 1, wherein said pool of target nucleic acids comprises fluorescently labeled nucleic acids.

19. The method of claim 1, wherein said detecting comprises quantifying fluorescence of a label on said hybridized nucleic acids at a spatial resolution of 100 $\mu$m or higher.

20. The method of claim 19, wherein said quantification is by means of a scanning confocal fluorescence microscope.

21. The method of claim 1, wherein said providing comprises:
   (i) hybridizing a pool of RNAs with a pool of oligonucleotides having the same sequences as said oligonucleotide probes to form a pool of hybridized nucleic acids;
   (ii) treating said pool of hybridized nucleic acids with RNase A, thereby digesting single stranded nucleic acid sequences and leaving intact the hybridized double stranded regions;
   (iii) denaturing the hybridized double-stranded regions and removing said oligonucleotides thereby leaving a pool of RNAs enhanced for those RNAs complementary to the oligonucleotide probes in said high density array.

22. The method of claim 1, wherein said providing comprises:
   (a) hybridizing a pool of RNAs with paired target specific oligonucleotides wherein said paired target specific oligonucleotides are complementary to regions on either side of a subsequence, said subsequence being complementary to at least one of said oligonucleotide probes in said array;
   (b) treating said pool of nucleic acids with RNase H to digest the hybridized (double stranded) nucleic acid sequences;

(c) isolating the remaining nucleic acid sequences having a length about equivalent to said subsequence.

23. The method of claim 1, wherein said providing comprises:
(a) hybridizing a pool of poly A+ mRNAs with oligonucleotides that hybridize specifically with preselected mRNA target messages;
(b) treatng said pool of nucleic acids with RNase H to digest the hybridized (double stranded) nucleic acid sequences thereby separating the coding sequence from the polyA+ tail;
(c) isolating or ampifying the re polyA+ RNA in said pool.

24. A method of identifying oligonucleotide probes to quantify the expression of a target nucleic acid, comprising:
providing a high density array of oligonucleotide probes, said array comprising a multiplicity of oligonucleotide probes, wherein each probe is complementary to a subsequence of said target nucleic acid and for each probe there is a corresponding mismatch control probe;
hybridizing said target nucleic acid to said array of oligonucleotide probes; and
identifying those probes for which the difference in hybridization signal intensity between each probe and its mismatch control is detectable.

25. The method of claim 24, further comprising:
hybridizing said probes identified for which the difference in hybridization signal intensity between each probe and its mismatch control is detectable to a pool of nucleic acids comprising nucleic acids other than said target nucleic acids; and
identifying probes having the lowest hybridization signal, wherein both the probe and its mismatch control have a hybridization intensity equal to or less than 10 times background.

26. The method of claim 24, wherein said oligonucleotide probes ranges in length from about 10 to about 50.

27. The method of claim 24, wherein said oligonucleotide probes are all the same length.

28. The method of claim 24, wherein said difference in hybridization intensity between each probe and its mismatch control is at least 10% of a background signal.

29. The method of claim 24, wherein said multiplicity of probes includes all the probes of a single length that are exactly complementary to a subsequence of said target nucleic acid, and wherein said probes have a length between about 5 and 50 nucleotides.

30. The method of claim 24, wherein said array comprises more than 100 different oligonucleotides wherein each different oligonucleotide is localized in a predetermined region of said surface and the density of said different oligonucleotides is greater than about 60 different oligonucleotides per 1 cm² of said surface.

31. The method of claim 24, wherein hybridization is performed with a fluid volume of about 250 µl or less.

32. The method of claim 24, wherein said target nucleic acid is a nucleic acid comprising at least a partial sequence or complementary sequence of a gene.

33. The method of claim 24, wherein said oligonucleotide probes are synthesi zed by light-directed polymer synthesis.

34. The method of claim 24, wherein said mismatch control probes have a centrally l ocated 1 base mismatch.

35. The method of claim 24, wherein said hybridization comprises hybridization at low stringency of 30° C. to 50° C. and 6 X SSPE-T or lower followed by one or more washes at progressively increasing stringency until a desired level of hybridization specificity is obtained.

36. The method of claim 25, wherein the sequences of the nucleic acids in said pool comprise the sequences of said probes.

37. The method of claim 2, wherein said oligonucleotide probes present in said array are oligonucleotide probes identified by the steps comprising:
providing a high density array of oligonucleotide probes, said array comprising a multiplicity of oligonucleotide probes, wherein each probe is complementary to a subsequence of said target nucleic acid and for each probe there is a corresponding mismatch control probe;
hybridizing said target nucleic acid to said array of oligonucleotide probes; and
identifying those probes for which the difference in hybridization signal intensity between each probe and its mismatch control is detectable.

38. The method of claim 2, wherein said oligonucleotide probes analyzed in said quantifying step are identified by the steps comprising:
providing a high density array of oligonucleotide probes, said array comprising a multiplicity of oligonucleotide probes, wherein each probe is complementary to a subsequence of said target nucleic acid and for each probe there is a corresponding mismatch control probe;
hybridizing said target nucleic acid to said array of oligonucleotide probes; and
identifying those probes for which the difference in hybridization signal intensity between each probe and its mismatch control is detectable.

39. A method of identifg polynucleotide probes to quantify the expression of a target nucleic acid, comprising:
providing a high density array comprising polynucleotide probes complementary to a subsequence of said target nucleic acid, wherein for each of said probes there is a corresponding mismatch control probe on said array;
hybridizing said array to a pool of nucleic acids comprising nucleic acids other than said target nucleic acids; and
identifying probes having a hybridization intensity equal to or less than a background intensity, wherein at least one of said probes chosen is used to quantify said expression of said target nucleic acid.

40. The method of claim 39, further comprising after said identifying step:
hybridizing said probes identified to said target nucleic acid; and
identifiing those probes for which the difference in hybridization signal intensity between each probe and its mismatch control is detectable.

41. The method of claim 1, wherein at least some of said oligonucleotide probes are from about 10 to about 40 nucleotides in length.

42. The method of claim 1, wherein at least some of said oligonucleotide probes are from about 15 to 40 nucleotides in length.

43. The method of claim 1, wherein at least some of said oligonucleotides are up to about 500 nucleotides in length.

44. The method of claim 1, wherein at least some of said oligonucleotides are greater than 10 nucleotides in length.

45. The method of claim 1, wherein at least some of said oligonucleotides are greater than 15 nucleotides in length.

* * * * *